US008165830B2

(12) United States Patent
McAnally et al.

(10) Patent No.: US 8,165,830 B2
(45) Date of Patent: Apr. 24, 2012

(54) METER ELECTRONICS AND METHODS FOR DETERMINING A PHASE DIFFERENCE BETWEEN A FIRST SENSOR SIGNAL AND A SECOND SENSOR SIGNAL OF A FLOW METER

(75) Inventors: Craig B McAnally, Thornton, CO (US); Denis M Henrot, Louisville, CO (US)

(73) Assignee: Micro Motion, Inc., Boulder, CO (US)

( * ) Notice: Subject to any disclaimer, the term of this patent is extended or adjusted under 35 U.S.C. 154(b) by 47 days.

(21) Appl. No.: 12/088,613

(22) PCT Filed: Oct. 16, 2006

(86) PCT No.: PCT/US2006/040232
§ 371 (c)(1),
(2), (4) Date: Mar. 28, 2008

(87) PCT Pub. No.: WO2007/047524
PCT Pub. Date: Apr. 26, 2007

(65) Prior Publication Data
US 2008/0252283 A1   Oct. 16, 2008

Related U.S. Application Data

(60) Provisional application No. 60/727,889, filed on Oct. 18, 2005.

(51) Int. Cl.
*G01F 1/00* (2006.01)
*G06F 19/00* (2011.01)
*G06F 17/40* (2006.01)

(52) U.S. Cl. ............ 702/54; 137/551; 702/45; 702/189; 708/105

(58) Field of Classification Search .............. 702/45, 702/48, 50, 54–56, 137, 1, 33, 127, 189; 73/861.01, 861.04, 861.18, 200, 198, 570, 73/649, 650, 861, 861.19, 861.351, 861.354, 73/861.355, 861.356, 861.357; 137/551; 708/100, 105, 131, 160
See application file for complete search history.

(56) References Cited

U.S. PATENT DOCUMENTS 4,187,721 A * 2/1980 Smith ................. 73/861.356
(Continued)

FOREIGN PATENT DOCUMENTS
JP         7181069 A       7/1995
(Continued)

OTHER PUBLICATIONS

Coupe F G A : "Digital Frequency Discriminator" Electronics Letters, IEE Stevenage, GB, vol. 15, No. 16, Aug. 2, 1979 pp. 489-490, XP000761150 ISSN: 0013-5194 the whole document.

*Primary Examiner* — Edward Cosimano
(74) *Attorney, Agent, or Firm* — The Ollila Law Group LLC

(57) ABSTRACT

Meter electronics (20) for processing sensor signals in a flow meter is provided according to an embodiment of the invention. The meter electronics (20) includes an interface (201) for receiving a first sensor signal and a second sensor signal and a processing system (203) in communication with the interface (201) and configured to receive the first sensor signal and the second sensor signal, generate a ninety degree phase shift from the first sensor signal, and compute a frequency from the first sensor signal and the ninety degree phase shift. The processing system (203) is further configured to generate sine and cosine signals using the frequency, and quadrature demodulate the first sensor signal and the second sensor signal using the sine and cosine signals in order to determine the phase difference.

11 Claims, 7 Drawing Sheets

U.S. PATENT DOCUMENTS

| | | | | | |
|---|---|---|---|---|---|
| RE31,450 | E | * | 11/1983 | Smith | 73/861.356 |
| 4,477,773 | A | * | 10/1984 | Margerum | 324/76.41 |
| 4,491,025 | A | * | 1/1985 | Smith et al. | 73/861.355 |
| 4,675,614 | A | * | 6/1987 | Gehrke | 327/3 |
| 4,914,956 | A | * | 4/1990 | Young et al. | 73/861.356 |
| 5,027,662 | A | * | 7/1991 | Titlow et al. | 73/861.356 |
| 5,069,074 | A | * | 12/1991 | Young et al. | 73/861.356 |
| 5,535,622 | A | * | 7/1996 | Walter | 73/121 |
| 6,154,021 | A | * | 11/2000 | Bergman et al. | 324/76.22 |
| 6,318,156 | B1 | * | 11/2001 | Dutton et al. | 73/61.44 |
| 6,505,131 | B1 | | 1/2003 | Henrot | |
| 6,505,519 | B2 | | 1/2003 | Henry et al. | |
| 6,507,791 | B2 | * | 1/2003 | Henry et al. | 702/45 |
| 7,062,976 | B2 | * | 6/2006 | Gysling et al. | 73/861.18 |
| 7,117,104 | B2 | * | 10/2006 | Urdaneta et al. | 702/48 |
| 7,805,261 | B2 | * | 9/2010 | Bell et al. | 702/45 |
| 7,908,097 | B2 | * | 3/2011 | Duffill et al. | 702/45 |
| 7,974,792 | B2 | * | 7/2011 | Duffill et al. | 702/45 |
| 7,983,855 | B2 | * | 7/2011 | Cunningham et al. | 702/45 |
| 7,996,160 | B2 | * | 8/2011 | McAnally et al. | 702/45 |
| 2002/0038186 | A1 | * | 3/2002 | Henry et al. | 702/45 |
| 2002/0183951 | A1 | | 12/2002 | Cunningham et al. | |
| 2005/0288873 | A1 | * | 12/2005 | Urdaneta et al. | 702/45 |
| 2008/0184814 | A1 | * | 8/2008 | Bell et al. | 73/861.356 |
| 2008/0184815 | A1 | * | 8/2008 | Bell et al. | 73/861.356 |
| 2008/0189067 | A1 | * | 8/2008 | Duffill et al. | 702/113 |
| 2008/0189079 | A1 | * | 8/2008 | McAnally et al. | 702/190 |
| 2008/0190195 | A1 | * | 8/2008 | Duffill et al. | 73/32 A |
| 2008/0223148 | A1 | * | 9/2008 | Cunningham et al. | 73/861.356 |
| 2008/0243400 | A1 | * | 10/2008 | Bell et al. | 702/45 |
| 2010/0198531 | A1 | * | 8/2010 | Bell et al. | 702/45 |
| 2011/0166801 | A1 | * | 7/2011 | Cunningham et al. | 702/45 |

FOREIGN PATENT DOCUMENTS

| | | | |
|---|---|---|---|
| RU | 2234682 | C2 * | 9/2003 |
| SU | 1471145 | A1 | 4/1989 |
| WO | WO-00/34748 | A2 | 6/2000 |
| WO | WO-2006/071454 | A | 7/2006 |

\* cited by examiner

METER ELECTRONICS AND METHODS FOR DETERMINING A PHASE DIFFERENCE BETWEEN A FIRST SENSOR SIGNAL AND A SECOND SENSOR SIGNAL OF A FLOW METER

The present application claims the benefit of expired. U.S. Provisional Patent Application No. 60/727,889, entitled "Meter Electronics and Methods for Determining Phase Difference Between a First Sensor Signal and a Second Sensor Signal of a Flow Meter", filed on Oct. 18, 2005.

BACKGROUND OF THE INVENTION

1. Field of the Invention

The present invention relates to meter electronics and methods for determining a phase difference between a first sensor signal and a second sensor signal of a flow meter.

2. Statement of the Problem

It is known to use Coriolis mass flow meters to measure mass flow, density, and volume flow and other information of materials flowing through a pipeline as disclosed in U.S. Pat. No. 4,491,025 issued to J. E. Smith, et al. of Jan. 1, 1985 and Pat. No. Re. 31,450 to J. E. Smith of Feb. 11, 1982. These flow meters have one or more flow tubes of different configurations. Each conduit configuration may be viewed as having a set of natural vibration modes including, for example, simple bending, torsional, radial and coupled modes. In a typical Coriolis mass flow measurement application, a conduit configuration is excited in one or more vibration modes as a material flows through the conduit, and motion of the conduit is measured at points spaced along the conduit.

The vibrational modes of the material filled systems are defined in part by the combined mass of the flow tubes and the material within the flow tubes. Material flows into the flow meter from a connected pipeline on the inlet side of the flow meter. The material is then directed through the flow tube or flow tubes and exits the flow meter to a pipeline connected on the outlet side.

A driver applies a force to the flow tube. The force causes the flow tube to oscillate. When there is no material flowing through the flow meter, all points along a flow tube oscillate with an identical phase. As a material begins to flow through the flow tube, Coriolis accelerations cause each point along the flow tube to have a different phase with respect to other points along the flow tube. The phase on the inlet side of the flow tube lags the driver, while the phase on the outlet side leads the driver. Sensors are placed at different points on the flow tube to produce sinusoidal signals representative of the motion of the flow tube at the different points. The phase difference between the two sensor signals is proportional to the mass flow rate of the material flowing through the flow tube or flow tubes. In one prior art approach either a Discrete Fourier Transform (DFT) or a Fast Fourier Transform (FFT) is used to determine the phase difference between the sensor signals. The phase difference, and a vibrational frequency response of the flow tube assembly, are used to obtain the mass flow rate.

In one prior art approach, an independent reference signal is used to determine a pickoff signal frequency, such as by using the frequency sent to the vibrational driver system. In another prior art approach, the vibrational response frequency generated by a pickoff sensor can be determined by centering to that frequency in a notch filter, wherein the prior art flowmeter attempts to keep the notch of the notch filter at the pickoff sensor frequency. This prior art technique works fairly well under quiescent conditions, where the flow material in the flowmeter is uniform and where the resulting pickoff signal frequency is relatively stable. However, the phase measurement of the prior art suffers when the flow material is not uniform, such as in two-phase flows where the flow material comprises a liquid and a solid or where there are air bubbles in the liquid flow material. In such situations, the prior art determined frequency can fluctuate rapidly. During conditions of fast and large frequency transitions, it is possible for the pickoff signals to move outside the filter bandwidth, yielding incorrect phase and frequency measurements. This also is a problem in empty-full-empty batching, where the flow meter is repeatedly operated in alternating empty and full conditions. Also, if the frequency of the sensor moves rapidly, a demodulation process will not be able to keep up with the actual or measured frequency, causing demodulation at an incorrect frequency. It should be understood that if the determined frequency is incorrect or inaccurate, then subsequently derived values of density, volume flow rate, etc., will also be incorrect and inaccurate. Moreover, the error can be compounded in subsequent flow characteristic determinations.

In the prior art, the pickoff signals can be digitized and digitally manipulated in order to implement the notch filter. The notch filter accepts only a narrow band of frequencies. Therefore, when the target frequency is changing, the notch filter may not be able to track the target signal for a period of time. Typically, the digital notch filter implementation takes 1-2 seconds to track to the fluctuating target signal. Due to the time required by the prior art to determine the frequency, the result is not only that the frequency and phase determinations contain errors, but also that the error measurement encompasses a time span that exceeds the time span during which the error and/or two-phase flow actually occur. This is due to the relative slowness of response of a notch filter implementation.

The result is that the prior art flowmeter cannot accurately, quickly, or satisfactorily track or determine a pickoff sensor frequency during two-phase flow of the flow material in the flowmeter. Consequently, the phase determination is likewise slow and error prone, as the prior art derives the phase difference using the determined pickoff frequency. Therefore, any error in the frequency determination is compounded in the phase determination. The result is increased error in the frequency determination and in the phase determination, leading to increased error in determining the mass flow rate. In addition, because the determined frequency value is used to determine a density value (density is approximately equal to one over frequency squared), an error in the frequency determination is repeated or compounded in the density determination. This is also true for a determination of volume flow rate, where the volume flow rate is equal to mass flow rate divided by density.

Because the phase difference can be derived using the determined frequency, an improved frequency determination can provide a fast and reliable phase difference determination.

SUMMARY OF THE SOLUTION

The above and other problems are solved and an advance in the art is achieved through the provision of meter electronics and methods for determining a phase difference between a first sensor signal and a second sensor signal of a flow meter.

Meter electronics for determining a phase difference between a first sensor signal and a second sensor signal of a flow meter is provided according to an embodiment of the invention. The meter electronics comprises an interface for receiving the first sensor signal and the second sensor signal and a processing system in communication with the interface. The processing system is configured to receive the first sensor signal and the second sensor signal, generate a ninety degree phase shift from the first sensor signal, and compute a frequency from the first sensor signal and the ninety degree phase shift. The processing system is further configured to generate sine and cosine signals using the frequency, and quadrature demodulate the first sensor signal and the second sensor signal using the sine and cosine signals in order to determine the phase difference.

A method for determining a phase difference between a first sensor signal and a second sensor signal of a flow meter is provided according to an embodiment of the invention. The method comprises receiving the first sensor signal and the second sensor signal, generating a ninety degree phase shift from the first sensor signal, and computing a frequency from the first sensor signal and the ninety degree phase shift. The method further comprises generating sine and cosine signals using the frequency. The method further comprises quadrature demodulating the first sensor signal and the second sensor signal using the sine and cosine signals in order to determine the phase difference.

A method for determining a phase difference between a first sensor signal and a second sensor signal of a flow meter is provided according to an embodiment of the invention. The method comprises receiving the first sensor signal and the second sensor signal, generating a ninety degree phase shift from the first sensor signal, and computing a frequency from the first sensor signal and the ninety degree phase shift. The method further comprises generating sine and cosine signals using the frequency. The method further comprises quadrature demodulating the first sensor signal and the second sensor signal using the sine and cosine signals, with the quadrature demodulating generating a first demodulated signal and a second demodulated signal. The method further comprises filtering the first demodulated signal and the second demodulated signal in order to remove high frequency components and cross-correlating the first demodulated signal and the second demodulated signal in order to determine the phase difference.

ASPECTS OF THE INVENTION

In one aspect of the meter electronics, the processing system is further configured to compute one or more of a mass flow rate, a density, or a volume flow rate using one or more of the frequency and the phase difference.

In one aspect of the meter electronics, the processing system is further configured to compute the ninety degree phase shift using a Hilbert transform.

In yet another aspect of the meter electronics, the quadrature demodulation generates a first demodulated signal and a second demodulated signal and the processing system is further configured to filter the first demodulated signal and the second demodulated signal in order to remove high frequency components and cross-correlate the first demodulated signal and the second demodulated signal in order to determine the phase difference.

In one aspect of the method, the method further comprises computing one or more of a mass flow rate, a density, or a volume flow rate using one or more of the frequency and the phase difference.

In another aspect of the method, the method further comprises computing the ninety degree phase shift using a Hilbert transform.

In yet another aspect of the method, the quadrature demodulation generates a first demodulated signal and a second demodulated signal and the quadrature demodulation further comprises filtering the first demodulated signal and the second demodulated signal in order to remove high frequency components and cross-con-elating the first demodulated signal and the second demodulated signal in order to determine the phase difference.

DESCRIPTION OF THE DRAWINGS

The same reference number represents the same element on all drawings.

DETAILED DESCRIPTION OF THE INVENTION

FIGS. 1-7 and the following description depict specific examples to teach those skilled in the art how to make and use the best mode of the invention. For the purpose of teaching inventive principles, some conventional aspects have been simplified or omitted. Those skilled in the art will appreciate variations from these examples that fall within the scope of the invention. Those skilled in the art will appreciate that the features described below can be combined in various ways to form multiple variations of the invention. As a result, the invention is not limited to the specific examples described below, but only by the claims and their equivalents.

Figure 1:
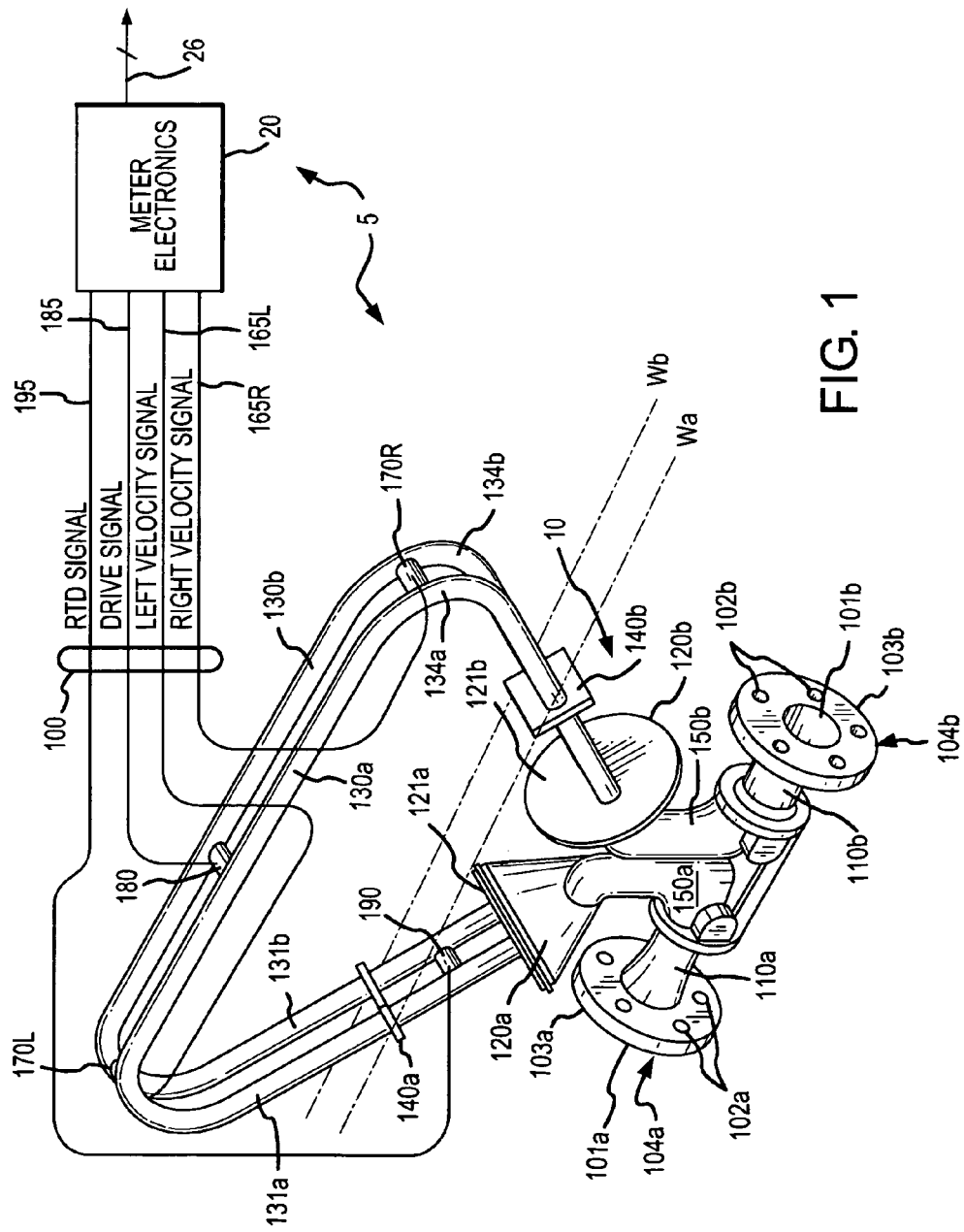
FIG. 1 illustrates a Coriolis flow meter in an example of the invention.

FIG. 1 shows a Coriolis flow meter 5 comprising a meter assembly 10 and meter electronics 20. Meter assembly 10 responds to mass flow rate and density of a process material. Meter electronics 20 is connected to meter assembly 10 via leads 100 to provide density, mass flow rate, and temperature information over path 26, as well as other information not relevant to the present invention. A Coriolis flow meter structure is described although it is apparent to those skilled in the art that the present invention could be practiced as a vibrating tube densitometer without the additional measurement capability provided by a Coriolis mass flow meter.

Meter assembly 10 includes a pair of manifolds 150a and 150b, flanges 103a and 103b having flange necks 110a and 110b a pair of parallel flow tubes 130a and 130b, drive mechanism 180, temperature sensor 190, and a pair of velocity sensors 170L and 170S. Flow tubes 130a acid 130b have two essentially straight inlet legs 131a and 131b and outlet legs 134a and 134b which converge towards each other at flow tube mounting blocks 120a and 120b. Flow tubes 130a and 130b bend at two symmetrical locations along their length and are essentially parallel throughout their length. Brace bars 140a and 140b serve to define the axis Wa and Wb about which each flow tube oscillates.

The side legs 131a, 131b and 134a, 134b of flow tubes 130a and 130b are fixedly attached to flow tube mounting blocks 120a and 120b and these blocks, in turn, are fixedly attached to manifolds 150a and 150b. This provides a continuous closed material path through Coriolis meter assembly 10.

When flanges 103a and 103b, having holes 102a and 102b are connected, via inlet end 104a and outlet end 104b into a process line (not shown) which can the process material that is being measured, material enters end 104a of the meter through an orifice 101a in flange 103a is conducted through manifold 150a to flow tube mounting block 120a having a surface 121a. Within manifold 150a the material is divided and routed through flow tubes 130a and 130b. Upon exiting flow tubes 130a and 130b, the process material is recombined in a single stream within manifold 150b including a mounting block 120b having a surface 121b and is thereafter routed to exit end 104b connected by flange 103b and orifice 101b having bolt holes 102b to the process line (not shown).

Flow tubes 130a and 130b are selected and appropriately mounted to the flow tube mounting blocks 120a and 120b so as to have substantially the same mass distribution, moments of inertia and Young's modulus about bending axes Wa-Wa and Wb-Wb, respectively. These bending axes go through brace bars 140a and 140b. Inasmuch as the Young's modulus of the flow tubes change with temperature, and this change affects the calculation of flow and density, resistive temperature detector (RID) 190 is mounted to flow tube 103b, to continuously measure the temperature of the flow tube. The temperature of the flow tube and hence the voltage appearing across the RID for a given current passing therethrough is governed by the temperature of the material passing through the flow tube. The temperature dependent voltage appearing across the RID is used in a well known method by meter electronics 20 to compensate for the change in elastic modulus of flow tubes 130a and 130b due to any changes in flow tube temperature. The RTD is connected to meter electronics 20 by lead 195.

Both flow tubes 130a and 130b are driven by driver 180 in opposite directions about their respective bending axes Wa and Wb and at what is termed the first out-of-phase bending mode of the flow meter. This drive mechanism 180 may comprise any one of many well known arrangements, such as a magnet mounted to flow tube 130b and an opposing coil mounted to flow tube 130a and through which an alternating current is passed for vibrating both flow tubes. A suitable drive signal applied by meter electronics 20, via lead 185, to drive mechanism 180.

Meter electronics 20 receives the RTD temperature signal on lead 195, and the left and right velocity signals appearing on leads 165L and 165R, respectively. Meter electronics 20 produces the drive signal appearing on lead 185 to drive element 180 and vibrate tubes 130a and 130b. Meter electronics 20 processes the left and right velocity signals and the RTD signal to compute the mass flow rate and the density of the material passing through meter assembly 10. This information, along with other information, is applied by meter electronics 20 over path 26 to utilization means 29.

Figure 2:
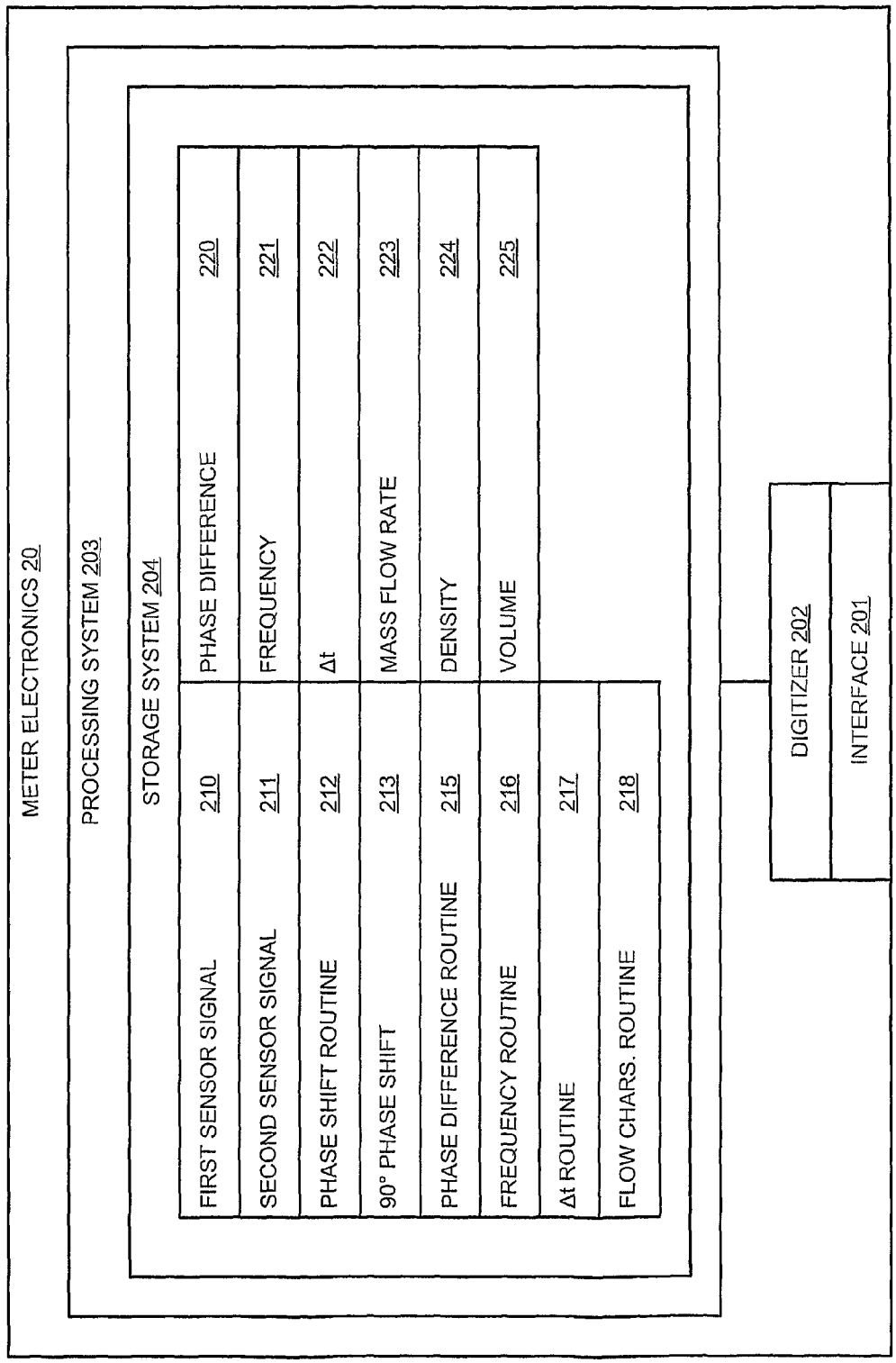
FIG. 2 shows meter electronics according to an embodiment of the invention.

FIG. 2 shows meter electronics 20 according to an embodiment of the invention. The meter electronics 20 can include an interface 201 and a processing system 203. The meter electronics 20 receives first and second sensor signals 210 and 211 from the meter assembly 10, such as pickoff/velocity sensor signals. The meter electronics 20 can operate as a mass flow meter or can operate as a densitometer, including operating as a Coriolis flow meter. The meter electronics 20 processes the first and second sensor signals 210 and 211 in order to obtain flow characteristics of the flow material flowing through the meter assembly 10. For example, the meter electronics 20 can determine one or more of a phase difference, a frequency, a time difference ($\Delta t$), a density, a mass flow rate, and a volume flow rate from the sensor signals, for example. In addition, other flow characteristics can be determined according to the invention. The determinations are discussed below.

The phase difference determination and the frequency determination are much faster and more accurate and reliable than such determinations in the prior art. This advantageously reduces the processing time required in order to compute the flow characteristics and increases the accuracy of both flow characteristics. Consequently, both the frequency and the phase difference can be determined much faster than in the prior art.

The prior art frequency determination methods typically take 1-2 seconds to perform. In contrast, the frequency determination according to the invention can be performed in as little as 50 milliseconds (ms). Even faster frequency determination is contemplated, depending on the type and configuration of the processing system, the sampling rate of the vibrational response, the filter sizes, the decimation rates, etc. At the 50 ms frequency determination rate, the meter electronics 20 according to the invention can be about 40 times faster than the prior art.

The interface 201 receives the sensor signal from one of the velocity sensors 170L and 170R via the leads 100 of FIG. 1. The interface 201 can perform any necessary or desired signal conditioning, such as any manner of formatting, amplification, buffering, etc. Alternatively, some or all of the signal conditioning can be performed in the processing system 203.

In addition, the interface 201 can enable communications between the meter electronics 20 and external devices. The interface 201 can be capable of any manner of electronic, optical, or wireless communication.

The interface 201 in one embodiment is coupled with a digitizer 202, wherein the sensor signal comprises an analog sensor signal. The digitizer 202 samples and digitizes the analog sensor signal and produces a digital sensor signal. The digitizer 202 can also perform any needed decimation, wherein the digital sensor signal is decimated in order to reduce the amount of signal processing needed and to reduce the processing time. The decimation will be discussed in more detail below.

The processing system 203 conducts operations of the meter electronics 20 and processes flow measurements from the flow meter assembly 10. The processing system 203 executes one or more processing routines and thereby processes the flow measurements in order to produce one or more flow characteristics.

The processing system 203 can comprise a general purpose computer, a microprocessing system, a logic circuit, or some other general purpose or customized processing device. The processing system 203 can be distributed among multiple processing devices. The processing system 203 can include any manner of integral or independent electronic storage medium, such as the storage system 204.

The processing system 203 processes the first sensor signal 210 and the second sensor signal 211 in order to determine one or more flow characteristics. The one or more flow characteristics can include a phase difference, a frequency, a time difference ($\Delta t$), a mass flow rate, and/or a density for the flow material, for example.

In the embodiment shown, the processing system 203 determines the flow characteristics from the two sensor signals 210 and 211 and a single 90 degree phase shift 213. The processing system 203 can determine at least the phase difference and the frequency from the two sensor signals 210 and 211 and the single 90 degree phase shift 213. In addition, the processing system 203 can further determine a phase difference, a time difference (Δt), and/or a mass flow rate for the flow material, among other things.

The storage system 204 can store flow meter parameters and data, software routines, constant values, and variable values. In one embodiment, the storage system 204 includes routines that are executed by the processing system 203. In one embodiment, the storage system 204 stores a phase shift routine 212, a phase difference routine 215, a frequency routine 216, a time difference (Δt) routine 217, and a flow characteristics routine 218.

In one embodiment, the storage system 204 stores variables used to operate a flow meter, such as the Coriolis flow meter 5. The storage system 204 in one embodiment stores variables such as the first sensor signal 210 and the second sensor signal 211, which are received from the velocity/pickoff sensors 170L and 170R. In addition, the storage system 204 can store a 90 degree phase shift 213 that is generated in order to determine the flow characteristics.

In one embodiment, the storage system 204 stores one or more flow characteristics obtained from the flow measurements. The storage system 204 in one embodiment stores flow characteristics such as a phase difference 220, a frequency 221, a time difference (Δt) 222, a mass flow rate 223, a density 224, and a volume flow rate 225.

The phase shift routine 212 performs a 90 degree phase shift on an input signal, i.e., on the sensor signal 210. The phase shift routine 212 in one embodiment implements a Hilbert transform (discussed below).

The phase difference routine 215 determines a phase difference using quadrature demodulation. Additional information can also be used in order to compute the phase difference. The phase difference in one embodiment is computed from the first sensor signal 210, the second sensor signal 211, and the frequency 221. The determined phase difference can be stored in the phase difference 220 of the storage system 204. The phase difference, when determined using the determined frequency 221, can be calculated and obtained much faster than in the prior art. This can provide a critical difference in flow meter applications having high flow rates or where multi-phase flows occur.

The frequency routine 216 determines a frequency (such as that exhibited by either the first sensor signal 210 or the second sensor signal 211) from the 90 degree phase shift 213. The determined frequency can be stored in the frequency 221 of the storage system 204. The frequency, when determined from the single 90 degree phase shift 213 and the sensor signal 210 or 211, can be calculated and obtained much faster than in the prior art. This can provide a critical difference in flow meter applications having high flow rates or where multi-phase flows occur.

The time difference (Δt) routine 217 determines a time difference (Δt) between the first sensor signal 210 and the second sensor signal 211. The time difference (Δt) can be stored in the time difference (Δt) 222 of the storage system 204. The time difference (Δt) comprises substantially the determined phase divided by the determined frequency, and is therefore used to determine the mass flow rate.

The flow characteristics routine 218 can determine one or more flow characteristics. The flow characteristics routine 218 can use the determined phase difference 220 and the determined frequency 221, for example, in order to accomplish these additional flow characteristics. It should be understood that additional information may be required for these determinations, such as the mass flow rate or density, for example. The flow characteristics routine 218 can determine a mass flow rate from the time difference (Δt) 222 and therefore from the phase difference 220 and the frequency 221. The formula for determining mass flow rate is given in U.S. Pat. No. 5,027,662 to Titlow et al., and is incorporated herein by reference. The mass flow rate is related to the mass flow of flow material in the meter assembly 10. Likewise, the flow characteristics routine 218 can also determine the density 224 and/or the volume flow rate 225. The determined mass flow rate, density, and volume flow rate can be stored in the mass flow rate 223, the density 224, and the volume 225 of the storage system 204, respectively. In addition, the flow characteristics can be transmitted to external devices by the meter electronics 20.

Figure 3:
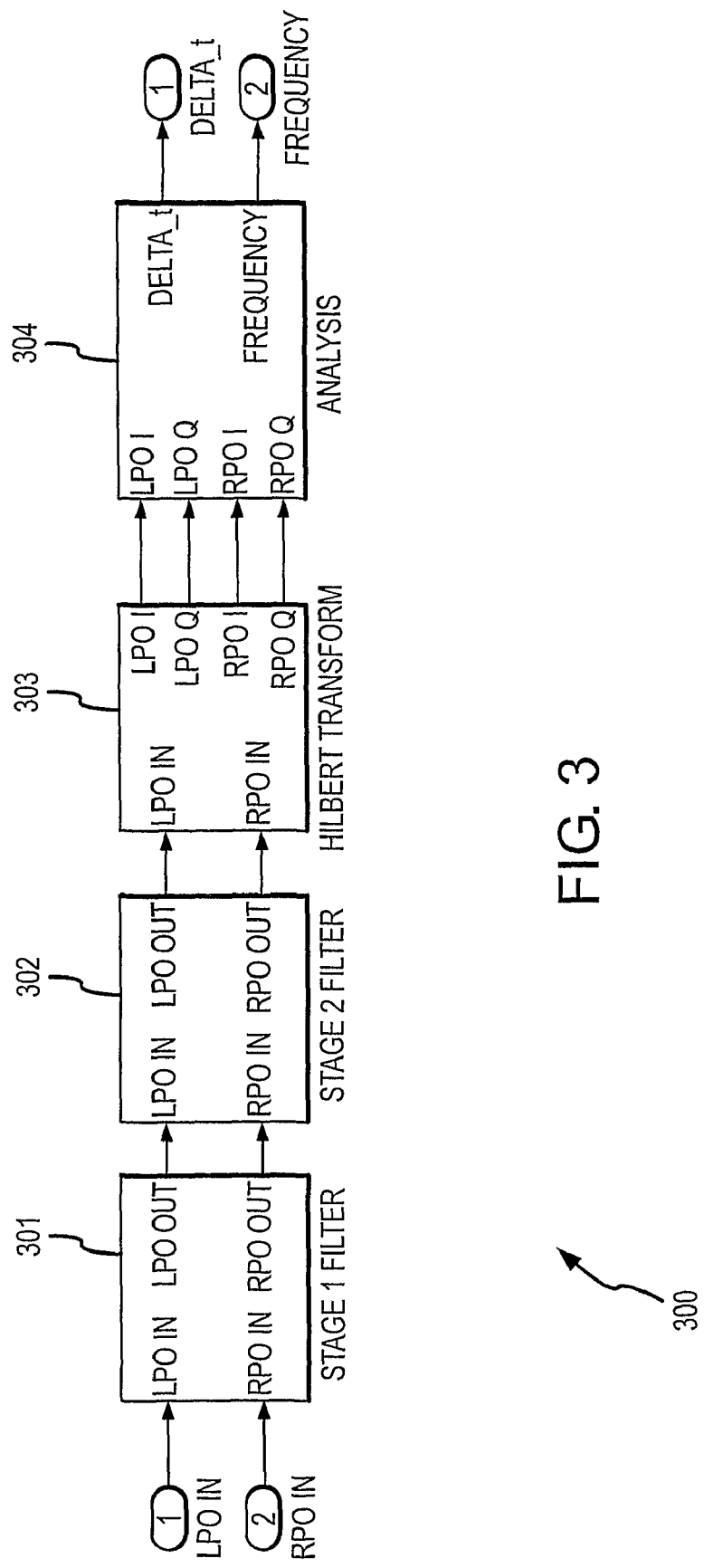
FIG. 3 is a block diagram of a portion of a processing system according to an embodiment of the invention.

FIG. 3 is a block diagram 300 of a portion of the processing system 203 according to an embodiment of the invention. In the figure, the blocks represent either processing circuitry or processing actions/routines. The block diagram 300 includes a stage 1 filter block 301, a stage 2 filter block 302, a Hilbert transform block 303, and an analysis block 304. The LPO and RPO inputs comprise the left pickoff signal input and the right pickoff signal input. Either the LPO or the RPO can comprise a first sensor signal.

In one embodiment, the stage 1 filter block 301 and the stage 2 filter block 302 comprise digital Finite Impulse Response (FIR) polyphase decimation filters, implemented in the processing system 203. These filters provide an optimal method for filtering and decimating one or both sensor signals, with the filtering and decimating being performed at the same chronological time and at the same decimation rate. Alternatively, the stage 1 filter block 301 and the stage 2 filter block 302 can comprise Infinite Impulse Response (IIR) filters or other suitable digital filters or filter processes. However, it should be understood that other filtering processes and/or filtering embodiments are contemplated and are within the scope of the description and claims.

Figure 4:
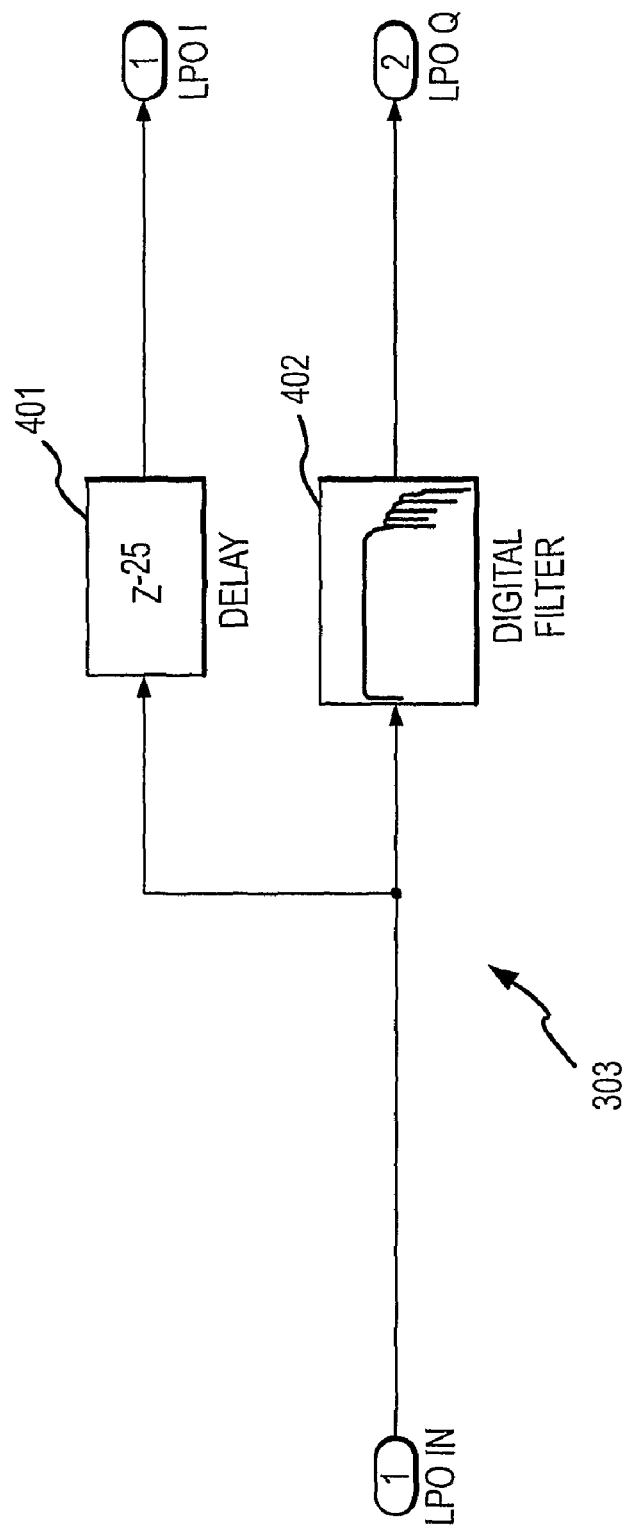
FIG. 4 shows detail of a Hilbert transform block according to an embodiment of the invention.

FIG. 4 shows detail of the Hilbert transform block 303 according to an embodiment of the invention. In the embodiment shown, the Hilbert transform block 303 includes a LPO delay block 401 in parallel with a LPO filter block 402. The LPO delay block 401 introduces a sampling delay. The LPO delay block 401 therefore selects LPO digital signal samples that are chronologically later in time that the LPO digital signal samples that are filtered by the LPO filter block 402. The LPO filter block 402 performs a 90 degree phase shift on the inputted digital signal samples.

The Hilbert transform block 303 is a first step to providing the phase measurement. The Hilbert transform block 303 receives the filtered, decimated LPO and RPO signals and performs a Hilbert transform. The Hilbert transform produces 90 degree phase-shifted versions of the LPO signal. The output of the Hilbert transform block 303 therefore provides the new quadrature (Q) component LPO Q, along with the original, in-phase (I) signal components LPO I.

The input to the Hilbert transform block 303 can be represented as:

$$\text{LPO} = A_{lpo} \cos(\omega t) \tag{1}$$

Using the Hilbert transform the output becomes:

$$\text{LPO}_{Hilbert} = A_{lpo} \sin(\omega t) \tag{2}$$

Combining the original terms with the output of the Hilbert transform yields:

$$\text{LPO} = A_{lpo}[\cos(\omega t) + i \sin(\omega t)] = A_{lpo} e^{j(\omega t)} \tag{3}$$

Figure 5:
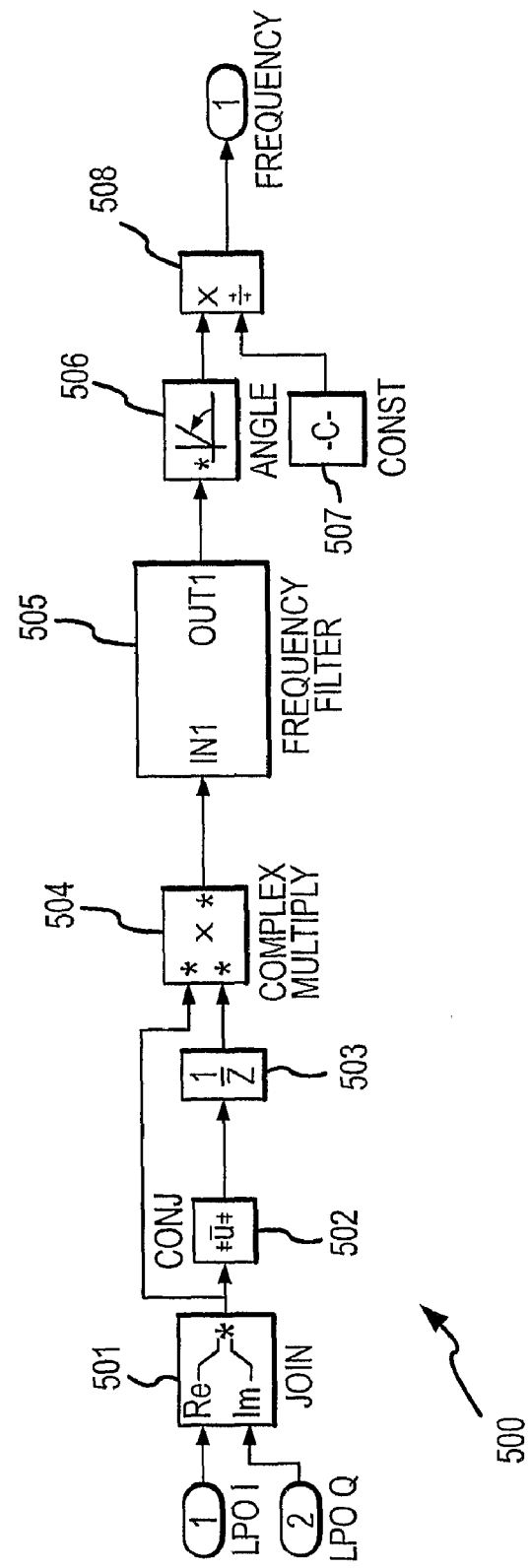
FIG. 5 is a block diagram of a frequency portion of an analysis block according to an embodiment of the invention.

FIG. 5 is a block diagram of a frequency portion 500 of the analysis block 304 according to an embodiment of the invention. The analysis block 304 in the embodiment shown is the final stage of the frequency and delta T (Δt) measurements. In the embodiment shown, the frequency portion 500 determines a frequency from the in-phase (I) and quadrature (Q) components of a single sensor signal. The frequency portion 500 can operate on either the left or right pickoff signal (LPO or RPO). In the embodiment shown, the frequency portion 500 operates on the LPO signal. The frequency portion 500 in the embodiment shown includes a join block 501, a complex conjugate block 502, a sampling block 503, a complex multiplication block 504, a filter block 505, a phase angle block 506, a constant block 507, and a division block 508.

The join block 501 receives both in-phase (I) and quadrature (Q) components of a sensor signal and passes them on. The conjugate block 502 performs a complex conjugate on a sensor signal, here the LPO signal. The delay block 503 introduces a sampling delay and therefore selects a digital signal sample that is chronologically older in time. This older digital signal sample is multiplied with the current digital signal in the complex multiplication block 504. The complex multiplication block 504 multiplies the LPO signal and the LPO conjugate signal, implementing equation (4) below. The filter block 505 implements a digital filter, such as the FIR filter previously discussed. The filter block 505 can comprise a polyphase decimation filter that is used to remove harmonic content from the in-phase (I) and quadrature (Q) components of the sensor signal, as well as to decimate the signal. The filter coefficients can be chosen to provide decimation of the inputted signal, such as decimation by a factor of 10, for example. The phase angle block 506 determines a phase angle from the in-phase (I) and quadrature (Q) components of the LPO signal. The phase angle block 506 implements a portion of equation (5) below. The constant block 507 supplies a factor comprising a sample rate $F_s$ divided by two pi ($\pi$), as shown in equation (6). The division block 508 performs the division operation of equation (6).

The frequency processing implements the following equation:

$$\overline{LPO}_{(n-1)} \times LPO_{(n)} = A_{lpo} e^{-j(\omega t_{-1})} \times A_{Lpo} e^{j(\omega t)} = A^2{}_{lpo} e^{j(\omega t - \omega t_{-1})} \quad (4)$$

The angle between two consecutive samples is therefore:

$$\omega t - \omega t_{-1} = \tan^{-1}\left[\frac{\sin(\omega t - \omega t_{-1})}{\cos(\omega t - \omega t_{-1})}\right] \quad (5)$$

which is the radian frequency of the left pick-off. Converting to Hz:

$$f_{lpo} = \frac{(\omega t - \omega t_{-1}) \times Fs}{2\pi} \quad (6)$$

Here "Fs" is the rate of the Hilbert transform block 303. In the example previously discussed, "Fs" is about 2 kHz.

Figure 6:
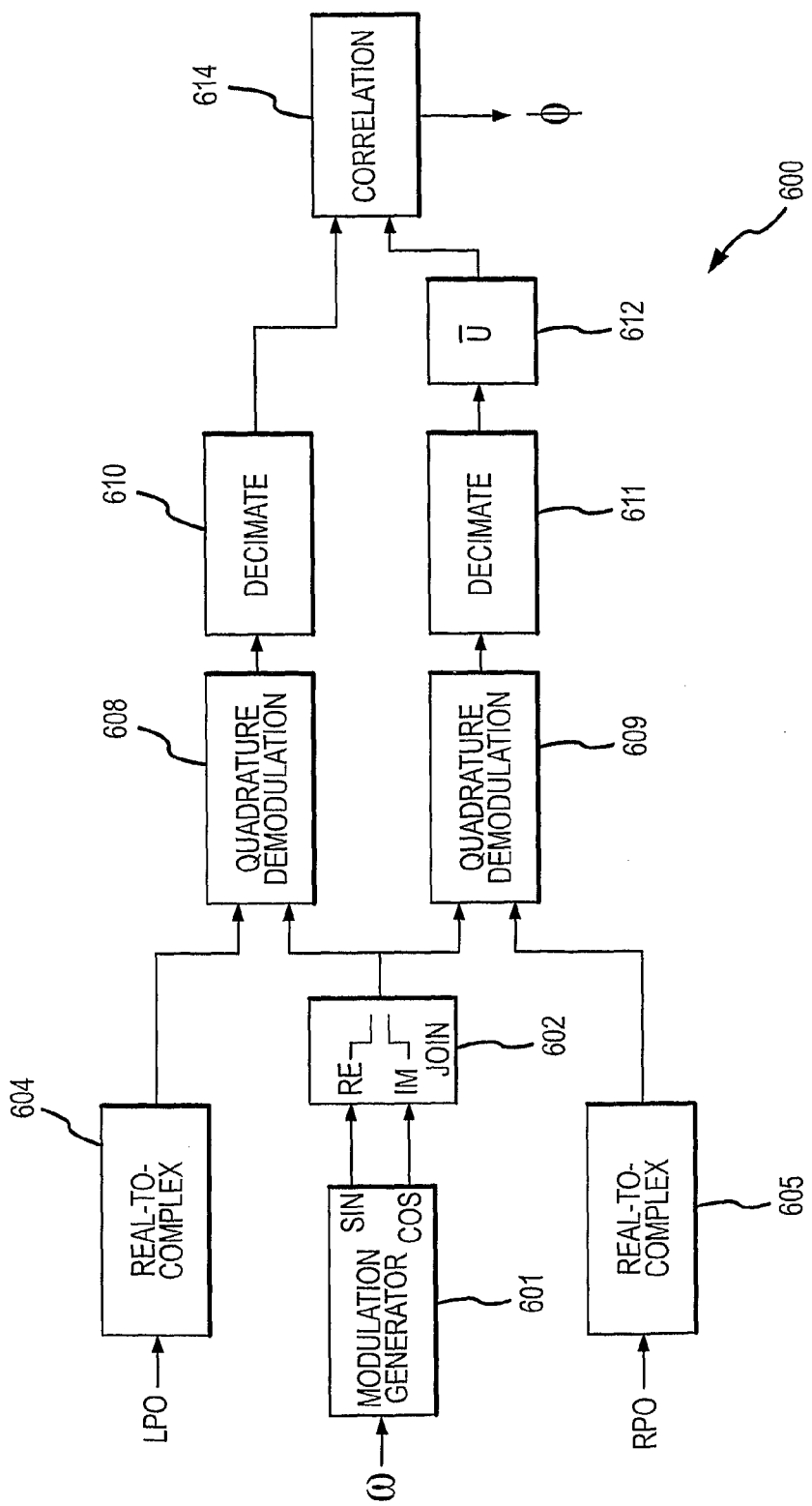
FIG. 6 is a block diagram of a phase difference portion of the analysis block according to an embodiment of the invention.

FIG. 6 is a block diagram of a phase difference portion 600 of the analysis block 304 according to an embodiment of the invention. The phase difference portion 600 outputs a phase difference between the LPO input signal and the RPO input signal. The phase difference portion 600 can be included in the analysis block 304 along with the frequency portion 500 of FIG. 5. In the figure, the blocks represent either processing circuitry or processing actions/routines. The phase difference portion 600 includes a modulation generator block 601, a join block 602, real-to-complex blocks 604 and 605, quadrature demodulation blocks 608 and 609, decimation blocks 610 and 611, a conjugate block 612, and a correlation block 614.

The modulation generator block 601 generates sin and cosine terms from the radian frequency value (ω) that is output by the frequency portion 500. The modulation generator block 601 therefore receives a frequency reference from the frequency portion 500. Because the frequency portion 500 can be obtained much faster and more reliably than in the prior art, consequently the phase difference determination can be also obtained much faster and more reliably than in the prior art. The sin and cosine terms comprise in-phase (I) and quadrature (Q) components of the frequency reference. The sin and cosine terms generated by the modulation generator block 601 are inputted into the join block 602.

The join block 602 receives the in-phase (I) and quadrature (Q) components from the modulation generator block 601. The join block 602 joins the in-phase (I) and quadrature (Q) components and passes them on to the quadrature demodulation blocks 608 and 609.

The real-to-complex blocks 604 and 605 generate imaginary (i.e., quadrature) components of the LPO and RPO input signals. The resulting in-phase (real) and quadrature (imaginary) components comprise sinusoids that includes both sine and cosine components. The real-to-complex blocks 604 and 605 pass the resulting in-phase (real) and quadrature (imaginary) components of both signals to the corresponding quadrature demodulation blocks 608 and 609.

The quadrature demodulation blocks 608 and 609 demodulate the LPO signal and the RPO signal using the sinusoids. The demodulation generates a first demodulated signal and a second demodulated signal. In addition, this demodulation produces a zero frequency component and a high frequency component for each of the LPO and the RPO. The high frequency component is later removed (see below). The output of the quadrature demodulation blocks 608 and 609 are passed to the decimation blocks 610 and 611, respectively.

The decimation blocks 610 and 611 can decimate the LPO and the RPO quadrature demodulation signals. For example, the decimation blocks 610 and 611 can decimate these two signals by a factor of about 10, for example. In addition, the decimation blocks 610 and 611 can perform any desired filtering of the demodulation signals. For example, in one embodiment the decimation blocks 610 and 611 can comprise a polyphase decimation filter that is used to remove harmonic content (i.e., the high frequency components) from the in-phase (I) and quadrature (Q) components of the sensor signal, as well as to decimate the signal. The filter coefficients can be chosen to provide decimation of the inputted signal, such as decimation by a factor of 10, for example. The decimation blocks 610 and 611 pass the demodulated RPO signal to the conjugate block 612 and pass the demodulated LPO signal to the correlation block 614.

The conjugate block 612 performs a complex conjugate on the demodulated RPO signal. The conjugate block 612 passes the conjugated demodulated RPO signal to the correlation block 614.

The correlation block 614 correlates the demodulated LPO and RPO signals. The conjugation operation followed by the correlation comprises a cross-correlation operation. The complex correlation can comprise a multiplication that produces a result shown in equations (17) and (18). As a result, the correlation block 614 produces the phase difference (or phase angle) value. The determined phase difference can be used to determine various flow characteristics. Because of the two separate quadrature demodulation processes shown in FIG. 6, the phase difference portion 600 can also be referred to as a quadrature demodulation chain.

Figure 7:
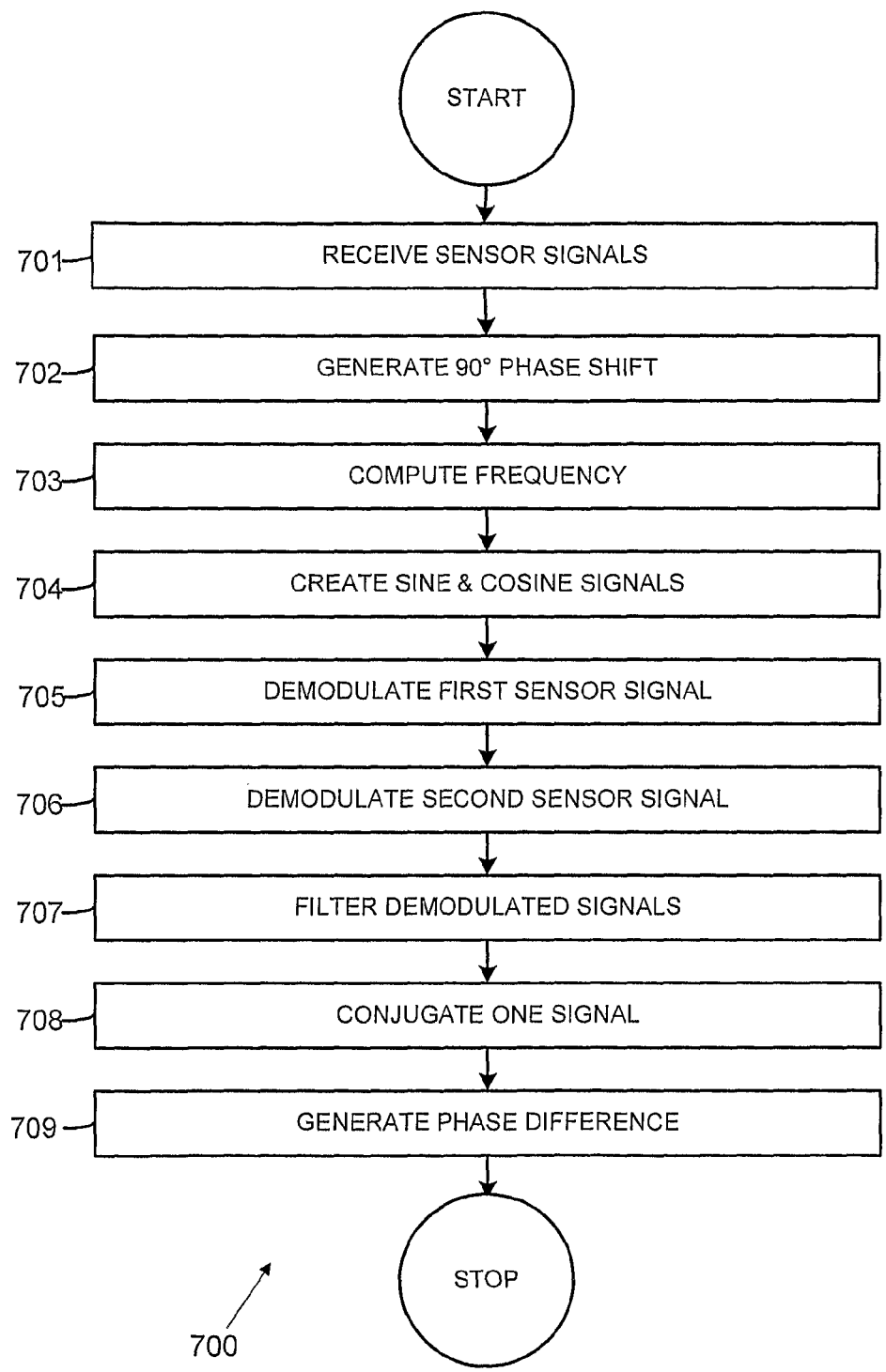
FIG. 7 is a flowchart of a phase difference quadrature demodulation method according to an embodiment of the invention.

FIG. 7 is a flowchart 700 of a phase difference quadrature demodulation method according to an embodiment of the invention. In step 701, the first and second sensor signals are received.

In step 702, a 90 degree phase shift is generated for one of the first or second sensor signals.

In step 703, a frequency (f) is determined from the 90 degree phase shift and the corresponding sensor signal. The frequency (f) can be represented as a radian frequency:

$$\omega = 2\pi f \qquad (7)$$

The determined frequency (f) can be used to determine flow characteristics. The determined frequency (f) can also be used to determine a phase difference between the first and second sensor signals, such as by using the QD chain method described above.

In step 704, a reference signal ($W_K$) is created. The reference signal ($W_K$) comprises a sine and cosine signal The reference signals ($W_K$) have the same frequency as the LPO and RPO signals. The radian frequency $\omega$ is operated on by a modulation generator in order to recursively generate the sinusoid demodulation reference signals ($W_K$), comprising:

$$W_k = \exp(-j\omega k) \qquad (8)$$

with the LPO and RPO input signals comprising:

$$x_{LPO}(k) = A\cos(\omega k + \phi_{LPo}) \qquad (9)$$

$$x_{RPO}(k) = A\cos(\omega k + \phi_{RPO}) \qquad (10)$$

In step 705, the sensor signal $x_{LPO}$ is demodulated with the reference signals $W_K$. The demodulation comprises mixing or multiplying the sensor signal $x_{LPO}$ with the reference signals $W_K$ in order to produce a demodulated LPO signal.

In step 706, the sensor signal $x_{RPO}$ is demodulated with the reference signals $W_K$. The demodulation comprises mixing or multiplying the sensor signal $x_{RPO}$ with the reference signals $W_K$ in order to produce a demodulated RPO signal.

As a result, the demodulated signals at the output of the quadrature demodulation blocks 608 and 609 comprise:

$$z_{LPO}(k) = W_k x_{LPO}(k) \qquad (11)$$

$$z_{RPO}(k) = W_k x_{RPO}(k) \qquad (12)$$

which can be re-written as:

$$z_{LPI}(k) = \frac{A}{2}\{\exp(j\phi_{LPO}) + \exp(-j(2\omega k + \phi_{LPO}))\} \qquad (13)$$

$$z_{RPO}(k) = \frac{A}{2}\{\exp(j\phi_{RPO}) + \exp(-j(2\omega k + \phi_{RPO}))\} \qquad (14)$$

In step 707, the demodulated signals are filtered in order to remove high frequency terms. These high frequency terms from the quadrature demodulation comprise the $[\exp(-j(2\omega k+\Phi_{LPO/RPO}))]$ terms in equations (13) and (14) above. A low-pass filter operation can be used to remove the high frequency terms. In one embodiment, the filtering can comprise an (I, Q) decimation X 40 dual cascade of decimation filters. The output of this filtering is represented by:

$$z_{LPO}(k) = \frac{A}{2}\exp(j\phi_{LPO}) \qquad (15)$$

$$z_{RPO}(k) = \frac{A}{2}\exp(j\phi_{RPO}) \qquad (16)$$

In step 708, one of the demodulated signals (such as the demodulated RPO signal in FIG. 6), is conjugated. The conjugation operation forms a negative of the imaginary signal.

In step 709, the filter outputs are correlated by a complex correlation stage. The conjugation and correlation steps of the complex correlation operation yield:

$$q(k) = z_{LPO}(k)\bar{z}_{RPO}(k) \qquad (17)$$

where the second z term represents the complex conjugation from step 708. It follows from equation (16) that the correlation/multiplication output comprises:

$$q(k) = \frac{A^2}{4}\exp(j(\phi_{LPO} - \phi_{RPO})) \qquad (18)$$

Consequently, the phase angle comprises:

$$\phi(k) = \arg(q(k)) = \phi_{LPO} - \phi_{RPO} \qquad (19)$$

The phase difference is therefore output.

The meter electronics and method for determining a phase difference between a first sensor signal and a second sensor signal of a flow meter according the invention can be implemented according to any of the embodiments in order to obtain several advantages, if desired. The invention can compute a phase difference from a determined frequency and the first and second sensor signals. The invention can provide a phase difference determination of greater accuracy and reliability. The invention can provide a phase difference determination faster than the prior art and while consuming less processing time.

We claim:

1. Meter electronics (20) for determining a phase difference between a first sensor signal and a second sensor signal of a flow meter, comprising:
   an interface (201) for receiving a first sensor signal and a second sensor signal; and
   a processing system (203) in communication with the interface (201) and configured to receive the first sensor signal and the second sensor signal, generate a ninety degree phase shift from the first sensor signal, compute a sensor signal frequency from the first sensor signal and the ninety degree phase shift, generate sine and cosine signals using the computed sensor signal frequency, and quadrature demodulate the first sensor signal and the second sensor signal using the sine and cosine signals in order to determine the phase difference between the first sensor signal and the second sensor signal.

2. The meter electronics (20) of claim 1, with the processing system (203) being further configured to compute one or more of a mass flow rate, a density, or a volume flow rate using one or more of the frequency and the phase difference.

3. The meter electronics (20) of claim 1, with the processing system (203) being further configured to compute the ninety degree phase shift using a Hilbert transform.

4. The meter electronics (20) of claim 1, wherein the quadrature demodulation generates a first demodulated signal and a second demodulated signal and with the processing system (203) being further configured to filter the first demodulated signal and the second demodulated signal in order to remove high frequency components and cross-correlate the first demodulated signal and the second demodulated signal in order to determine the phase difference.

5. A method for determining a phase difference between a first sensor signal and a second sensor signal of a flow meter, the method comprising:

receiving the first sensor signal and the second sensor signal;

generating a ninety degree phase shift from the first sensor signal;

computing a sensor signal frequency from the first sensor signal and the ninety degree phase shift;

generating sine and cosine signals using the computed sensor signal frequency; and quadrature demodulating the first sensor signal and the second sensor signal using the sine and cosine signals in order to determine the phase difference between the first sensor signal and the second sensor signal.

6. The method of claim 5, further comprising computing one or more of a mass flow rate, a density, or a volume flow rate using brie or more of the frequency and the phase difference.

7. The method of claim 5, further comprising computing the ninety degree phase shift using a Hilbert transform.

8. The method of claim 5, with the quadrature demodulating generating a first demodulated signal and a second demodulated signal, and with the quadrature demodulating further comprising:

filtering the first demodulated signal and the second demodulated signal in order to remove high frequency components; and cross-correlating the first demodulated signal and the second demodulated signal in order to determine the phase difference.

9. A method for determining a phase difference between a first sensor signal and a second sensor signal of a flow meter, the method comprising:

receiving the first sensor signal and the second sensor signal;

generating a ninety degree phase shift from the first sensor signal;

computing a sensor signal frequency from the first sensor signal and the ninety degree phase shift;

generating sine and cosine signals using the computed sensor signal frequency;

quadrature demodulating the first sensor signal and the second sensor signal using the sine and cosine signals, with the quadrature demodulating generating a first demodulated signal and a second demodulated signal;

filtering the first demodulated signal and the second demodulated signal in order to remove high frequency components; and cross-correlating the first demodulated signal and the second demodulated signal in order to determine the phase difference between the first sensor signal and the second sensor signal.

10. The method of claim 9, further comprising computing one or more of a mass flow rate, a density, or a volume flow rate using one or more of the frequency and the phase difference.

11. The method of claim 9, further comprising computing the ninety degree phase shift using a Hilbert transform.

* * * * *

UNITED STATES PATENT AND TRADEMARK OFFICE
CERTIFICATE OF CORRECTION

PATENT NO. : 8,165,830 B2
APPLICATION NO. : 12/088613
DATED : April 24, 2012
INVENTOR(S) : Craig B McAnally et al.

It is certified that error appears in the above-identified patent and that said Letters Patent is hereby corrected as shown below:

Column 5, line 8, replace "can" with --carries--

Column 5, lines 28, 31 and 34 replace "RID" with --RTD--

Column 13, line 15, replace "brie" with --one--

Signed and Sealed this
Twelfth Day of February, 2013

Teresa Stanek Rea
*Acting Director of the United States Patent and Trademark Office*